United States Patent [19]

Knuth et al.

[11] Patent Number: 5,057,424
[45] Date of Patent: Oct. 15, 1991

[54] FLAVOR COMPOSITION AND METHOD

[75] Inventors: Mark E. Knuth, San Carlos; Om P. Sahai, San Mateo, both of Calif.

[73] Assignee: Escagenetics Corporation, San Carlos, Calif.

[21] Appl. No.: 428,482

[22] Filed: Oct. 30, 1989

Related U.S. Application Data

[63] Continuation of Ser. No. 78,745, Jul. 28, 1987, abandoned.

[51] Int. Cl.$^5$ ............................ C12N 5/04; C12P 1/00
[52] U.S. Cl. ................................ 435/240.48; 435/41; 435/240.4
[58] Field of Search ........... 435/240.4, 240.46, 240.48, 435/41

[56] References Cited

FOREIGN PATENT DOCUMENTS 0052001  5/1982  European Pat. Off. .

OTHER PUBLICATIONS

Dziezak (4/86) Food Technology, pp. 122, 124–129.
Janet et al. (1984) Plant Genetic Resources Newsletter #57, pp. 25–27.
An Rao (1977) in J. Reinert & Y. P. S. Bajaj, eds., Plant Cell, Tissue, and Organ Culture, Springer-Verlog, New York, pp. 64–65.
Yamada et al. (1983) in D. A. Evans et al., Eds., Handbook of Plant Cell Culture, vol. 1, MacMillan Publ. Co., New York, pp. 717–728.
Tyler et al. (1981) Pharmacognosy, Lea and Febiger, Philadelphia, pp. 74–75.
Al-Abta et al., (1979) Plant Science Letters 16: 129–134.
Becker, (1970) Biochem Physiol Pflanz 161:425–441.
Collin et al., in Handbook of Plant Cell Culture, vol. 1, pp. 729–747 (D. Evans et al., eds 1983).
Dodds et al., in Plant Tissue Culture, pp. 54–69 and pp. 180–188 (Cambridge Univ. Press, 1985).
Dougall et al., in Adv. in Experimental Med. and Biol., vol. 118, pp. 135–152 (J. Petricciani et al., eds 1978).
Jalal et al., (1979) New Phytol 83:343–349.
Kireeva et al., (1978) Soviet Plant Physiol 25:438–443.
Knuth, Abstra Pap Am Chem Soc 190 (Sep. 8–13, 1985 meeting), No. 121.
Nagel et al., (1975) Planta Med 27:151–158.
Sarkar et al., (1976) J Agric Food Chem 24(2):317–320.
Selby et al., (1980) New Phytol 84:307–312.
Staba, (1963) Dev Microbiol 4:193–198.
Sugisawa et al., (1976) Agric Biol Chem 40:231–232.
Townsley, (1974) J Inst Can Sci Tech Alim 7:76–78.
Turnball et al., (1981) New Phytol 87:257–268.
Weiler, in Plant Tissue Culture and its Biotechnical Application, pp. 266–277 (W. Barz et al., eds 1977).
Yeoman et al., in Differentiation in Vitro, 4th Symposium Brit Soc Cell Biol, pp. 65–81 (Cambridge Univ Press, 1981).
Zenk, in Frontiers of Plant Tissue Culture, pp. 1–13 (Calgary Univ Press, 1978).

Primary Examiner—Elizabeth C. Weimar
Assistant Examiner—Che Swyden Chereskin
Attorney, Agent, or Firm—Peter J. Dehlinger

[57] ABSTRACT

A vanilla flavor composition is produced by vanilla-plant callus cells suspended in tissue culture, under conditions which promote secretion of vanilla flavor components into the culture medium. The flavor components may be separated from the medium by adsorption resins. Also disclosed are methods for preparing callus cells capable of secreting flavor components in tissue culture, and callus cells produced thereby.

3 Claims, 2 Drawing Sheets

FLAVOR COMPOSITION AND METHOD

This is a continuation of application Ser. No. 07/078,745 filed 07/28/87, now abandoned.

FIELD OF THE INVENTION

The present invention relates to plant-produced flavor compositions and methods, and in particular, to a vanilla flavor composition produced by plant cells in culture.

REFERENCES

Al-Abta, S., et al, Planta Med 42:236 (1979).
Berker, H., Biochem Physiol Pflanz 161:425 (1970).
Collin, H. A., et al in *Handbook of Plant Cell Culture*, Vol 1 (D. Evans et al, eds) Macmillan, pp. 729–747 (1983).
Dodds, J. H., et al, in *Plant Tissue Culture*, Cambridge Univ Press, pp. 54–69 and pp. 180–188 (1986).
Dougall, D. K., in *Adv in Experimental Med and Biol* (J. Petreciana et al, eds.) Plenum Press, pp. 136–151 (1980).
Jalal, M. A. F., et al, New Phytol 83:343 (1979).
Kireeva, S. A., et al, Soviet Plant Physiol 25:438 (1978).
Knuth, M., Abstra Pap Am Chem Soc, 190 (September 8–13, 1985 meeting).
Nagel, M., et al, Planta Med 27:151 (1975).
Sardesai, D. L., et al, J Food Sci 27:94 (1962).
Sarkar, K. S., et al, J Agric Food Chem 24(2):317 (1976).
Selby, C., et al, New Phytol 84:307 (1980).
Staba, E. J., Dev Microbiol 4 193 (1963).
Sugisawa, H., et al, Agric Biol Chem 40:231 (1976).
Szoeke, E., et al, Biochem Salgotarjan, 18th Hungary Ann Meeting 189 (1978).
Tounsley, P. M., J Inst Can Sci Tech Alim 7:76 (1974).
Turnball, A., et al, New Phytol 87:257 (1981).
Weiler, E. W., in *Plant Tissue Culture and its Bio-Technical Application* (W. Barz et al, eds) Springer-Verlag, pp 266–277 (1977).
Yeoman, M. M., et al in *Differentiation In Vitro, 4th Symposium Brit Soc Cell Biol*, Cambridge Univ Press, pp. 65–81 (1981).
Zenk, M. H., in *Frontiers of Plant Tissue Culture* (T. Thorpe, ed.), Calgary Univ Press, Calgary p. 1–13 (1978).

BACKGROUND OF THE INVENTION

Natural vanilla is a complex mixture of flavor components extracted from the beans of vanilla plants, usually *Vanilla fragrans*. The extraction process involves an initial curing process, during which vanilla-precursor glucosides in the bean break down to form natural vanillin (4-hydroxy-3-methoxybenzaldehyde) and related flavor components, followed by one or more alcohol extractions to remove the relatively hydrophobic flavor components from the bean. Each of these steps may be relatively time-consuming and costly. For example, the curing process typically is carried out by alternately sun-drying and fermenting the beans, followed by additional warehouse curing and dehydration. Total curing times of up to 4 months may be required to obtain the proper flavor and reduce moisture content to prevent molding. Following curing, the beans are crushed for extraction. Best results are obtained when the crushed beans are extracted with a series of progressively more dilute alcoholic solutions. Each extraction requires a minimum of about 5 days.

Because of the relatively high cost involved in growing, harvesting, and extracting vanilla beans, most vanilla flavor "extract" which is sold commercially is synthetic vanillin, made from wood pulp lignin or from clove oil. The synthetic flavor which makes up about 90% of the vanilla flavor market, however, lacks many of the secondary components which contribute to the quality of flavor and aroma of natural vanilla extract.

One potential alternative source of a complex vanilla flavor composition is plant cells or tissue grown in culture (Knuth). The possibility of obtaining secondary plant products, including plant flavor components, from cell or tissue culture has been previously proposed (Staba; Zenk; Dougall; Yeoman; Knuth; and Collin). This approach has been limited, however, by problems of obtaining suitable cell or tissue material for culturing. Studies with a variety of plant types, particularly those which produce essential flavor oils, such as lemon, mint, avocado, and herbs, such as anise, fennel, and sage, indicate that undifferentiated plant tissues are unable to produce the natural oils, possibly because the tissues lack oil glands, and/or because essential metabolic precursors are not produced (Collin). In cultured herb tissues, flavor components reappeared following redifferentiation into roots and shoots (Becker), and in both celery and onion, flavor components reappeared with redifferentiation (Al-Apta; Selby; Turnbull). Partially differentiated callus or suspension cultures from several flavor-producing plants also show synthesis of a variety of flavor components (Nagel; Szoeke; Sugisawa; Sardesai; Kireeva; Tounsley; and Jalal).

Related to this problem is the difficulty of obtaining cell or tissue material that can be expanded readily in culture, produces the secondary products in high yield, and is stable with long-term culturing. In particular, differentiated or partially differentiated cells generally do not grow well in culture. Even where such cells are obtained, the level of secondary product formation may be quite low compared with the natural plant, and therefore poorly competitive with natural flavor extraction methods.

The problem of obtaining flavor material in an easily isolatable form from cell culture has also limited the cell culture approach. In some cases, flavor component(s) may not be secreted from the culture cells, such that the flavor components must be harvested from the cell or tissue material. By way of example, U.S. Pat. No. 3,710,512 describes a method for producing a licorice extract-like material from cultured plant tissue cells suspended in a culture medium. Here the flavor composition is extracted by boiling the culture mix, to release the compound from the cells, filtering the boiled material, to remove cell debris, and concentrating the filtrate. It can be appreciated that product extraction is inefficient both because cells are lost and because the flavor material must be purified from total cell extract material.

In summary, although the possibility of obtaining flavor components in plant cell or tissue culture has been explored, difficulties in obtaining plant cell or tissue material which is capable of (a) growing readily in culture, over long periods, and (b) secreting desired flavor components in a form which allows isolation from the culture medium, have severely constrained this approach.

SUMMARY OF THE INVENTION

One general object of the invention is to provide plant cells capable of producing and secreting flavor components in culture.

A more specific object of the invention is to provide such cells which produce and secrete a complex vanilla flavor composition. A related object of the invention is to provide methods for obtaining callus cells which are capable of long-term growth in culture and which secrete flavor components into the culture medium in easily isolatable form.

Yet another object of the invention is to provide a plant cell culture system for use in the efficient production of vanilla flavor components.

Providing a novel vanilla flavor composition which is produced in cell culture is still another object of the invention.

The invention includes, in one aspect, a vanilla flavor composition produced in culture by callus cells which are derived from Vanilla plant tissue material, and selected for ability to propagate in plant liquid culture medium. The callus cells are cultured under conditions which promote secretion of vanilla flavor components into the growth medium, and the secreted flavor components are separated from the growth medium.

The callus cells may be prepared from tissue segments taken from the growing point of a *Vanilla* plant, such as *V. fragrans* or *V. phaeantha*, by first culturing the tissue segments on a solid support, in the presence of plant growth hormones, and selecting those tissue segments which show callus formation. The induced to rapid cell growth in cell culture, according to one feature of the invention, by first culturing the selected tissue segment in liquid medium, then culturing the segment on solid agar containing plant growth hormones, before dissociating the callus material into cell clumps for cell growth and vanilla flavor production in liquid culture. In one embodiment, the cells produced are derived from *V. fragrans* and have the characteristics of ATCC #40354. The cells may be further selected, e.g., by plating on solid agar medium, for high vanillin production.

According to another aspect of the invention, it has been discovered that vanilla flavor production is enhanced in a cell culture by continually removing flavor components from the culture medium. This can be done efficiently by contacting the culture medium with a polymeric hydrophobic adsorbents, such a phenolic resins, which adsorb the flavor components. The flavor components are easily extracted from the adsorbent.

One vanilla flavor composition which has been produced according to the invention has a ratio of vanillin to the combined amounts of vanillyl alcohol, 3,4-dihydroxybenzaldehyde, 4-hydroxybenzyl alcohol, and 4-hydroxybenzaldehyde, which is substantially greater than that of natural vanilla extract obtained from vanilla beans. This composition is also characterized by a ratio of vanillin to the combined amounts of flavor components which elute later than vanillin on an HPLC column eluted with a methanol/acetic acid gradient, which is substantially less than that of natural vanilla extract obtained from vanilla beans.

In another aspect, the invention includes callus cells which are (a) capable of growth in cell culture, (b) secrete a selected plant flavor component in the cell culture, and (c) are preferably undifferentiated. In one embodiment, which includes callus cells derived from vanilla plant tissue material, the amount of flavor material secreted in the cell culture is enhanced by removing the secreted flavor material from the culture medium as it is produced. An exemplary vanilla plant callus cell line has the characteristics of ATCC #40354.

Also forming part of the invention is a method and cell culture system for producing plant flavor composition. The system includes a culture chamber, where cell growth and flavor component production occur, and a separate extraction chamber where the flavor components are extracted from the medium, by circulating medium from the culture chamber through a polymeric hydrophobic adsorbent in the extraction chamber. The cells are preferably immobilized in the culture chamber, e.g., by cell immobilization on a porous substrate.

These and other objects and features of the invention will become more fully apparent when the following detailed description of the invention is read in conjunction with the accompanying drawings.

DETAILED DESCRIPTION OF THE INVENTION

I. Preparation of Callus Cells

Figure 1:
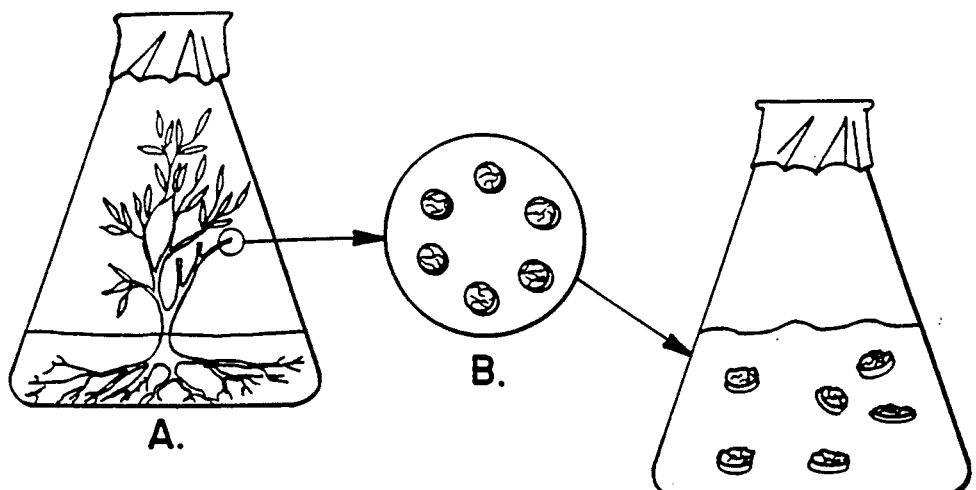
FIGS. 1A-1E illustrate plant tissue manipulation steps used in producing callus cell particles capable of secreting vanilla flavor components in liquid culture.

Part A below and Examples 1 and 2 below describe the preparation of callus cells drum the growing root tips of sterilized plants, according to a novel callus-induction method of the invention. In part B and Example 3, the preparation of callus cells from sterilized vanilla beans is described. Methods for selecting high-producer cells are considered in Part C.

A. Preparing Callus Cells from Growing Plant Tips

A variety of vanilla plant species, including *V. fragrans, V. phaeantha, V. pompona,* and *V. tahitensis,* may be used for preparation of callus cells, although *V. fragrans* and *V. phaeantha* are preferred. These plants may be obtained from commercial sources, such as the U.S.-D.A Research Station (Puerto Rico) or San Francisco State University.

A variety of other plants are known to produce vanilla and these may also be used as a source of plant material Included in this group are:
1. *Avena fatua* (Wild oat): hulls
2. *Oryza sativa* (Rice): straw
3. *Sorghum:* grains
4. *Hordeum vulgare* (Barley): cell walls
5. *Fagopyrum sagitatum* (Buckwheat): seeds
6. *Secale cereale* (Rye)
7. *Triticum aestivum* (Wheat): cell wall and leaves
8. *Zea mays* (Corns): cell wall
9. *Arachis hypogaea* (Peanuts): pods and ground nuts
10. *Coffea arabica* (Coffee): roots, leaves and seedlings
11. *Gossypium mexicanum* (Cotton): stalks
12. *Brassica napus* (Rapeseed): flour and hull
13. *Imperata cylindrica:* leaves
14. *Medicago arborea:* leaves and flower 15. *Veratrum album ssp.* labelianum: plants
16. *Subtropical grass:*
    *Acroceras macrum*
    *Chloris gayana*
    *Digitaria decumbens*
    *Panicum maximum*
    *Cortaderia selloana*
    *Cynodon dactylon*
    *Setaria sphacelata*
    *Tripsacum laxum*
    *Andropogon nodosum*
    *Brachiaria mutica*
    *Plicatulum paspalum*
    *Eragrostis curvula*
    *Cichorium intybus* (Chicory) roasted roots
17. *Parthenium argentatum* (Guayule)
18 *Pedalium murex:* leaves
19. *Vicia faba* (Fava beans)
20 *Phaseolus lunatus:* leaves
21. *Lycopersicum esculentum* (Tomato): cell walls
22. *Solanum tuberosum* (Potato): peels and wound-healed potato
23. *Cucurbita pepo* (Pumpkin): roots and colyledons
24. *Vaccinium macrocarpom* (Cranberries)
    *V. oxycocus*
25. *Vaccinium* myrtilus (Bilberry)
    *V. uliginosum* (Bog blueberry) (Blueberries)
    *V. corymbosum* (High-bush blueberry)
26. *Rubus chamaemorus* (Cloud berries)
27. *Castanea crenata*
28. *Carya pecan* (Pecan): kernels
    Tree nuts: nut meats and testae
    Pine nut, Almond, Filbert, American chestnut,
    A hybrid American chestnut, Chinese chestnut,
    Black walnut, Butter nut and Shagbark trickory
30. *Agave americana:* leaves
31. *Aganosma caryophyllata:* flowers
32. *Aristolochia mollissima:* stems and leaves
33. *Centaurium*
34. *Eicthornia crassipes* (Water hyacinth): leaves
35. *Iris germania:* rhizomes
36. Genus *Polygonum:* overground mass
    *P. weyrichi, P. panjutini, P. sachalinese,* and *P. cuspidutum*
37. Genus *Rosa* (Rose)
38. *Betula pendula* (Birch): bark
39. *Voandzeia subterranea* (Bambarra groundnut): seeds
40. *Cynanchum otophyllum:* roots
41. *Dendrocalamus strictus* (Bamboo)
42. *Diospyros kaki* (persimmon)
43. *Lycium chinese*
44. *Nectandra rigida*
45. *Quercus rubra* (Oak): leaves
46. *Opium poppy:* placenta
47. *Pinus sylvestris* (Scotch pine)
48. *Sarcandra glaber* and *N. spicatus*
49. *Viscum album* (Mistletoe)
50. *Xyris semifuscata*
51. *Chlorella pyrenoidosa* (Green algae)
52. *Phaeophyceae* (Brown algae)
53. Copper peat
54. Hardwood lignin sawdust To obtain sterilized, bacteria-free plants, the plants are grown to maturity under controlled greenhouse conditions, such as those described in Example 1. Vegetative shoots harvested from the plants, with leaves removed, are sterilized and cultured with repeated transfer on agar plates containing a suitable growth medium and an antibiotic. Explants which show no sign of contamination are grown under conditions which promote adventitious bud formation. Details of the procedure, which provided about 80% bacteria-free explants, are given in Example 1.

One preferred method for obtaining callus cells, according to the invention, is detailed in Example 2, and illustrated in FIG. 1. In this method aerial root tips are cut from the above sterilized explants (FIG. 1A), sterilized, and cut into 3–4 mm root sections which are then individually cultured on solid agar medium containing selected growth hormones. One optimal medium contains Murashige-Skoog (MS) medium (Dodds) supplemented with 1 ppm. each of 2,4-dichlorophenoxyacetic acid (2,4-D) and benzylacetic acid (BA).

The root sections are transferred 2–3 times onto the same medium, and the segments are examined for callus formation, as evidenced by formation of amorphous cell clumps on the cut surface of the segment, illustrated in FIG. 1B. Typically about 0.1% of the root sections which were handled in this way showed evidence of callus formation as detailed in Example 2A.

When the root sections with callus-like swellings from above are transferred directly into liquid culture medium, little or no cell growth is observed. According to one aspect of the invention, it has been discovered that callus cell growth in liquid culture can be induced by intermediate culture steps in which the selected tissue with callus-like swellings is first incubated in fresh liquid medium, in the presence of plant growth hormones, then cultured again on solid medium, with selection of those calli which shows active cell growth when recultured on solid medium as detailed in Examples 2B–2D.

In the first liquid-phase culture (Figure 1C), the callus-containing sections are suspended in a liquid growth medium, such as the one used for initial callus induction on solid agar. An exemplary growth hormone mix includes 1 ppm 2,4-D and BA. No callus growth is observed at this stage. After a 2–3 week culture period, the sections may be cultured 1–2 times more under the same conditions.

The root tip calli are now transferred to a second solid-medium culture (FIG. 1D) containing growth medium and a growth hormone mixture, as exemplified in Example 2. The calli are cultured on the medium typically 4–6 weeks, and transferred to fresh plates 1–4 times, until a significant increase in calli size, typically about 300%, is observed. The calli are now in an induced, undifferentiated state which allows rapid and stable cell growth in liquid culture containing growth hormones, and production of vanilla flavor products in a suitable culture medium.

To obtain an actively dividing cell culture in liquid medium, the calli from above are broken up as by mincing into relatively small pieces, which are then suspended in liquid growth medium (FIG. 1E), such as the one used in the second solid-medium culture, and the pieces are incubated with agitation until the calli gradually break down into small multi-cell clumps, typically containing 5–20 cells. Since the objective at this stage is to increase the cell biomass rapidly, the nutrient medium contains adequate carbon and nitrogen sources, as well as auxin and cytokinin growth hormones, such as 2,4-D and BA, as above. The cells are cultured under standard plant culture conditions until the cells reach the end of the logarithmic growth phase, typically at a cell concentration of about 7–8 g/l. The cells are now examined for cell viability, by uptake and cleavage of a fluorescent dye precursor. If more than about 25% of the cells are viable, the cells are reduced or concentrated by centrifugation, and resuspended in fresh growth medium, at a concentration of about 2-3 g/l. One cell line which has been prepared by this method has been deposited at the American Type Culture Collection, Rockville, MD, and has ATCC #40354.

The cells obtained in the method are classed as undifferentiated, on the basis of (a) rapid cell growth in culture and (b) lack of identifiable differentiated cell structures, as observed by light microscopy.

B. Preparing Callus From Seeds

Beans from vanilla plants, including the species listed above, are suitable for the present method, and can be obtained from the sources named above. Initially, the beans are sterilized, cut in half, and grown on suitable germination agar medium, such as the one used in Example 3. A portion of these seeds—typically about 5-10%—will germinate, as evidenced by the production of embryo and subsequent formation of a cone-shaped protocorm.

Continued growth of the germinated seeds, with transfer to fresh agar plates containing a suitable hormone-supplemented growth medium, such as described in Example 3, produces numerous rhizoids formed from the epidermal cells of the embryo and leaf primordia on top of the cone shaped protocorms. Segments of both the leaf primordia and rhizoid tip segments are individually cultured on agar plates containing the same callus induction medium described in part A above. The tissue pieces are cultured for about 3-4 weeks on the agar medium, then transferred onto similar culture plates an additional 1-4 times until callus formation occurs.

The calli may be teased apart and cultured directly in plant liquid growth medium like that above. Alternatively, in cases where cell growth is slow, the calli are preferably further induced through intermediate liquid culture and solid-medium culture steps like those used in the method of part A for stimulating callus cell growth in liquid culture. Liquid cultures of actively growing callus cells are grown to stationary phase, and tested for cell viability, as above. Viable cell cultures are subcultured to a desired cell density in the liquid medium.

C. Selecting High Flavor-Component Producers

The callus cells produced above can be further selected to obtain high producers of vanillin and/or other selected vanilla flavor components. The selection method may follow known radioimmunoassay (RIA) methods (Weiler), using radiolabel or fluorescent-label antibody methods to identify a selected flavor component, e.g., vanillin. Here the flavor component is attached to a carrier protein, for example keyhole limpet hemocyanin, and used to induce antibodies in an inoculated animal, yielding a serum antibody fraction that forms one of the reagents for the assay. The second reagent is a fluorescent-labeled anti-IgG antibody specific against the first-reagent antibodies. Thus, if the serum antibody fraction is obtained from goats, the second reagent is a labeled anti-goat IgG antibody. The second reagent is commercially available.

In the assay procedure, the cell or cell clumps from above are plated on solid agar medium containing suitable nutrients for vanillin production, as considered in Section II. After 1-2 days culture on the plates, the cell clumps are reacted with first-reagent serum antibody from above, to bind antibody to the plated cells in proportion to the amount of vanillin produced by the cells. Adding the second-reagent fluorescent-labeled antibody to the cells now labels the vanillin producers with a fluorescent tag. High producers are identified by high fluorescent levels.

Another type of cell selection procedure involves direct detection of vanillin or other vanilla-related product directly on the agar plates. One preferred assay for detection of vanilla is based on a modification of the vanilla test for flavinols. In an acid solution, vanilla is protonated to give a weak electrophilic radical which can react with a flavanoid, such as catechin, at the 6 or 8 ring position, to form a compound which turns red or pink on dehydration (Sarkar). The assay is applied in the present invention by first plating the cell clumps, at a suitable concentration, on a solid-agar nutrient medium (defined below), and allowing the cells to incubate under conditions of vanillin production. After a 1-2 day incubation period the plates are blotted with a filter paper to transfer cell products. The filter is then sprayed with a catechin reagent containing catechin in an acid solution, and dried by heating at temperatures below about 80° C. The intensity of red-colored spots on the dehydrated filter indicates the extent of vanillin production by the corresponding cell clumps. Those spots identified with highest vanillin production are then picked from the agar plate for further growth and/or cell selection.

II. Producing Vanilla Flavor Composition

A. Cell Culture Media

For producing vanilla flavor composition, the callus cells from above are cultured in liquid medium under conditions which are selected to maximize the amount of vanillin produced and/or to achieve a desired ratio of vanillin to one or more other vanilla flavor components. The principal variables in the medium which can be adjusted to improve yield of the desired vanilla composition are (a) nutrient, (b) plant hormones, and (c) vanilla component precursors. References which review the topic of secondary plant product formation in culture may be consulted for a more detailed discussion of factors which effect culture production (Collin, Dodds).

The nutrients which are present in the medium are preferably those supplied by any conventional plant medium, such as Murashige-Skoog medium, which has been modified to limit the nitrogen available to the cells. Typically, the usual ammonium salts used for plant growth medium are reduced or eliminated. Limiting the availability of nitrogen has the effect of inhibiting cell growth and therefore the resources of the cell which are devoted to cell growth alone. At the same time, since the vanilla flavor components do not contain nitrogen, production of the desired components is not inhibited.

The effect of plant hormones on production and composition of the vanilla components can be assessed by conventional methods. Experiments conducted in support of the present invention show that the hormone mix containing 2,4-D and BA used in callus cell production and growth are suitable for vanilla flavor production in culture medium. To determine other favorable hormone compositions, the hormone mix may be systematically adjusted to supplement or replace the existing individual hormones with one or more additional plant hormones. For example, 2,4-D may be replaced by indole 3-acetic acid (IAA) or other auxins. Similarly, BA may be replaced by kinetin, zeatin, or other cytokinens. The effects of other plant hormones, including gibberellins and ethylene, may be similarly examined. After altering hormone composition, the cells are cultured for a selected period, typically 2–5 days, and assayed for cell growth, and vanillin production and/or for relative amounts of selected vanilla-flavor components, the latter by HPLC methods detailed below and in Example 5. It should be borne in mind that a hormone regimen which produces cell differentiation may well alter the nature of the cells and their stability in culture.

A third factor influencing vanilla component production is the nature and concentration of vanilla component precursors in the medium. Experiments conducted in support of the present invention suggest that phenylalanine and ferulic acid, two metabolic precursors of vanillin, produce little enhancement in vanillin production by the callus cell culture. By contrast vanillyl alcohol, a biotransformation precursor of vanillin, does induce a significant increase in vanillin output. The cell culture method is also amenable to induction or inhibition of selected vanilla flavor components by addition of immediate precursors or metabolic inhibitors, to the medium.

It will also be recognized that temperature, light, pH and gas mixture may also be varied to alter vanilla flavor levels or composition.

In summary, one advantage of the present invention over plant extract methods is the ability to readily manipulate culture conditions to optimize production and/or the relative concentrations of flavor components.

B. Extracting Flavor Components

As indicated above, the callus cells in liquid culture secrete the desired flavor components into the culture medium, allowing the components to be extracted without loss of culture cells, and with a minimum of required purification. According to another important aspect of the invention, it has been discovered that vanilla component production is significantly enhanced by removing the flavor components from the medium during production of the components in culture. The greater production observed when the flavors are continuously removed from culture may be due to product instability in the medium and/or feedback inhibition of the product synthesis. One preferred method for removing flavor components in culture is to contact the medium continuously with a hydrophobic resin which selectively adsorbs vanilla flavor components.

Suitable resins for use in component extraction include polymeric hydrophobic adsorbents, such as XAD-4 XAD-7 (Rohm and Hass, Philadelphia, PA), having nonpolar phenolic groups capable of adsorbing the vanilla flavor components. XAD-4 is a nonpolar polystyrenedivinylbenzene resin which is supplied in particle-bead form with 20/50 mesh particle sizes.

In the simplest configuration, the particle resin is included in the culture reaction vessel. After culture, the beads are washed several times with distilled water, then extracted with an alcoholic solution, typically 50% alcohol, to remove the vanilla flavor components. Alternatively, the resin may be packed in a column, and the flavor components eluted with a solvent gradient, to obtain separate product components. The eluted flavor components can then be recovered in more concentrated form by solvent evaporation, if desired. The nature of the flavor components obtained in a typical culture production method, according to the invention, is described below.

In a second general method, cell culture production and product extraction are physically separate and the culture medium is periodically contacted with adsorbant material to remove accumulated flavor products. In a simple, discontinuous system, this can be done by applying a cell culture mixture periodically to a resin column, eluting unbound material with several washes of distilled water, and then eluting bound flavor material, as above, with an alcoholic solution or gradient. A continuous culture system, in which the callus cells are immobilized in a reaction chamber, and culture medium is continuously circulated through a resin bed is described below.

Vanilla flavor material may also be isolated from the culture cell mixture, or cell-free culture medium, by direct solvent extraction.

C. Continuous Culture System

Figure 2:
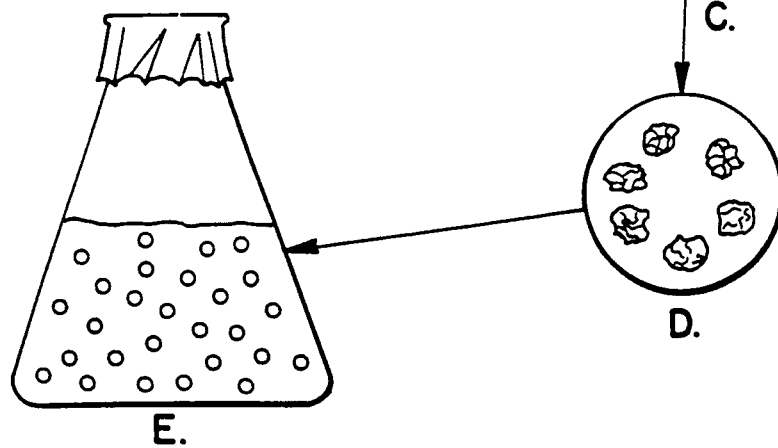
FIG. 2 is a diagrammatic representation of a reactor system used in producing vanilla flavor components, according to one aspect of the invention.
Figure 2:
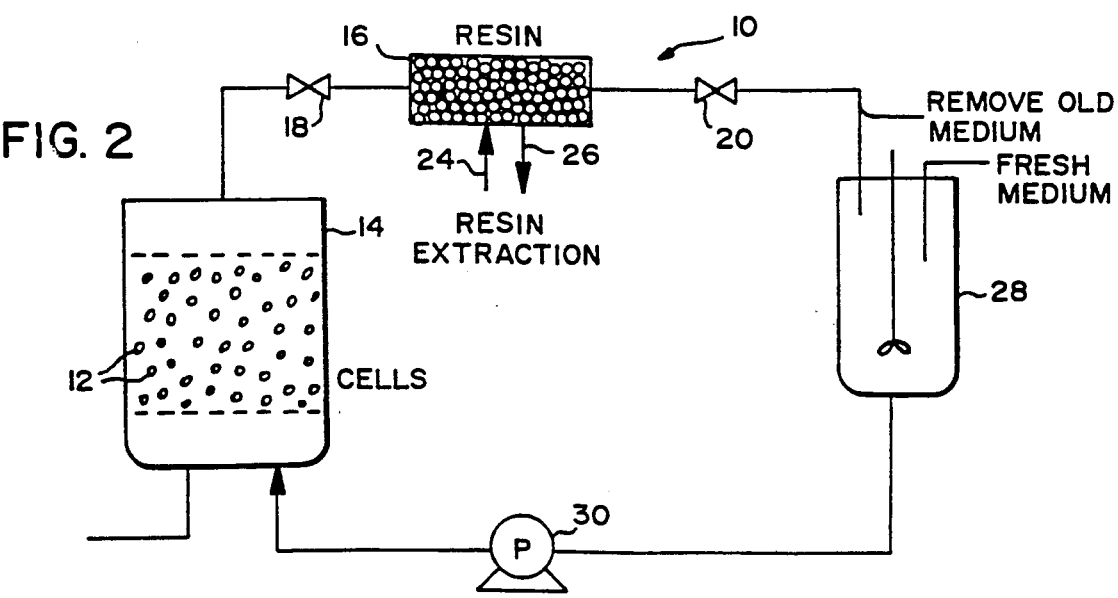

FIG. 2 illustrates, in simplified form, a culture system 10 designed for continuous, large-scale production of vanilla flavor composition, using the method of the invention. The callus cells in the system, here indicated at 12, are immobilized within a culture chamber 14 to allow circulation of culture medium through the chamber. A variety of methods are available for immobilizing the cells within the chamber. In one preferred method, the cells (or cell clumps) can be encapsulated or entrapped using polymeric matrices, such as agarose, agar, kappa-carageenen, or chitosan.

In another embodiment, the cells are confined within the chamber by suitable filtration means. This may include small-pore filters placed at the inflow and outflow ports of the chamber, or use of hollow fibers for cell culture, as described in U.S. Pat. No. 4,442,206.

Also contained in the system is a resin chamber 16 which is connected in-line with the culture chamber, through a valve 18, for extracting product carried in culture medium. Resin in chamber 16 is immobilized on a solid support conventionally. Flow of culture medium out of the chamber is through a valve 20. The cell product material bound to the resin is periodically extracted by closing valves 18, 20, and passing extraction solution through the chamber via extraction ports 24, 26.

Following product extraction in the resin chamber, a portion of the medium is removed, and the remainder flows into a mixing vessel 28, where the medium is mixed with fresh medium supplied to the system, as shown. From here, the medium is returned to the culture chamber, through a pump 30 which produces the circulation of medium in the system, preferably at a rate which circulates about 80% of the medium every hour. It will be appreciated that the system is equipped with temperature controls and gas supplies for maintaining the system at selected environment conditions.

III. Vanilla Flavor Composition

Figure 3A:
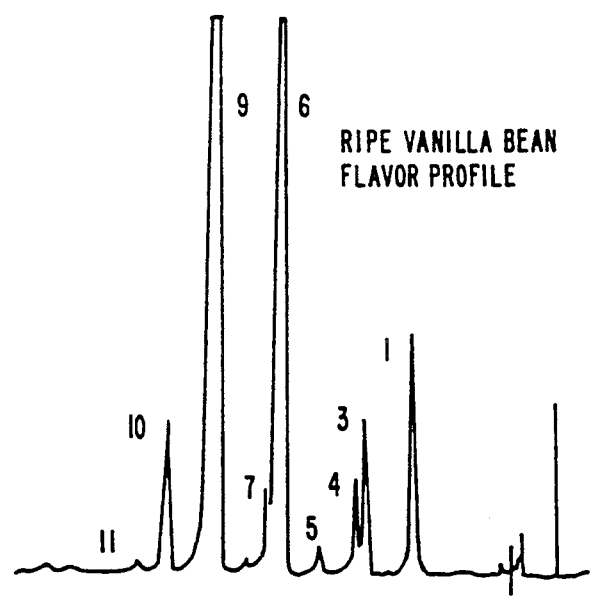
FIGS. 3A and 3B are HPLC chromatograms of vanilla flavor components of the invention (3A) and of natural vanilla extract obtained from vanilla beans.
Figure 3B:
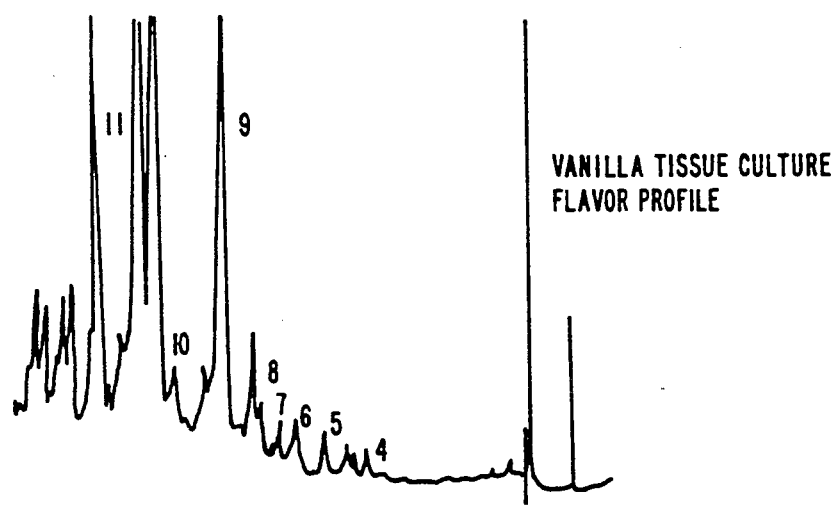

FIG. 3B shows an HPLC chromatogram of a typical vanilla flavor composition produced according to the invention, as detailed particularly in Example 5. HPLC chromatographic conditions are given in Example 7. As seen, the composition includes a predominant vanillin peak (peak 9), as well as several other peaks identified here: 3,4-dihydroxy benzaldehyde (peak 4) 4-hydroxy benzoic acid (peak 5), 4-hydroxy benzaldehyde (peak 6), vanillic acid (peak 7), caffeic acid (peak 8), coumaric acid (peak 10), and ferulic acid (peak 11). In addition, the composition contains a number of slower-euting components.

The HPLC profile of natural vanilla extract obtained from vanilla beans is shown in FIG. 3A. This composition also has a predominant vanillin peak, and includes the components identified with peaks 4-11 in FIG. 3B, as well as 4-hydroxybenzyl alcohol (peak 1) and vanillyl alcohol (peak 3). A comparison of the two compositions shows that the vanilla composition of the invention has a greater ratio of vanillin to the compounds corresponding to peaks 1-4 than the natural vanilla bean extract. On the other hand, the ratio of vanillin to slower migrating components (those eluting after vanillin on the HPLC column) is smaller in the composition of the invention than in the natural vanilla extract. These ratio comparisons are with reference to the HPLC chromatography conditions employed, as detailed in Example 7.

The HPLC analysis provides a convenient method for following changes in the relative amounts of components in the vanilla composition with changes in culturing conditions, such as variations in hormone, metabolic precursors, or nutrients in the culture medium. For example, to enhance the relative concentration of any selected component, the medium may be supplemented with precursor or inhibitor compounds, and the effect relative to the composition of the component easily assessed. Additionally, cells which secrete a desired ratio of flavor compounds can be selected on the basis of the HPLC profiles of their products. Also, chromatography can be used to achieve a desired purification of the composition, for example, to remove all or selected peaks which elute after the major vanillin peak.

The vanillin composition of the invention may be formulated as a vanilla flavor composition, preferably in an ethanolic solution similar to natural and artificial vanilla flavor compositions sold commercially. The flavor components can also be added to processed foods, such as baked goods, beverages, ice cream, and the like, for natural vanilla flavor.

From the foregoing, it can be appreciated how various objects and features of the invention have been achieved. The callus cells obtained using the novel plant tissue culture methods described in Section I have several advantageous features which are unexpected in view of earlier studies on secondary product production by cultured plant cells or tissues. In particular:

A. The flavor-producing cells are substantially undifferentiated, and therefore allow rapid cell increase in cell culture, for achieving a biomass adequate for large-scale vanilla flavor production.

B. The callus cells are stable in liquid cultures under both cell-growth and vanilla production conditions. Studies carried out in support of the invention show continued ability of vanilla cells to produce vanilla flavor components in subculture after several months, and the cells can be expanded in growth medium repeatedly without loss of vanilla flavor producing ability.

C. The cells produce a complex flavor mixture which contains all or most of the flavor components present in natural vanilla-bean extract.

D. The cells secrete the flavor components, allowing efficient isolation and purification of the composition without depleting either the cell medium or cells in the production culture.

According to another important feature of the invention, the amount of flavor composition produced can be enhanced significantly by removing flavor components from the medium as they are being produced. This can be done simply in a culture system in which the cell medium is circulated through a resin bed adapted to adsorb hydrophobic product compounds from the medium. The adsorbed material, in turn, can be readily extracted from the resin. This feature, and the ability to grow the cells rapidly and stably in culture, allow for efficient, and large-scale production of vanilla flavor compounds in culture. Further, the nature of the flavor composition can be altered, to enhance selected flavors and/or inhibit others, by varying culture conditions.

Finally, the callus cells can be selected for high production and/or enhanced production of specific flavor components by cell selection.

The following examples illustrate various methods of preparing callus tissue for vanilla composition production in culture, culture conditions for achieving production, and methods of obtaining the extract. The methods are intended to illustrate, but not limit the scope of the invention.

EXAMPLE 1

Propagation of Vanilla Plants

A. Establishing greenhouse plants

Two species of vanilla plants, *V. fragrans,* and *V. phaeantha,* were planted in a mixture of soil, peat moss, and milled bark (1:2:2 by volume). The vines were grown upright, with the aerial roots clinging to stakes and sphagnum-moss wall support. The vines were misted daily with a sprinkler system, and a complete fertilizer was applied once a month. The greenhouse humidity was maintained at between about 40-80%, and the temperature, between about 20°-29° C., taking care to avoid direct exposure to sunlight.

B. Sterilizing plant tissue

Vegetative shoots, about 5 cm in length, were harvested from the greenhouse plants, and the leaves removed from the shoots. After soaking the shoots in 1% Alconox for 20 minutes, with occasional shaking, and rinsing three times in distilled water, 3 mm shoot tips were removed by dissection, and the remaining shoot was cut into approximately 1.5 cm nodal segments, such that each segment includes one node. The shoot tips and nodal segments are placed upright in 1% agar containing MS (Murashige-Skoog) medium supplemented with 1 ppm BA (Medium A) and 500 ppm cefotoxime. Removing the epidermal layers of the nodal segments at this stage increased the number of bacteria-free tissue segments which were obtained. After culturing for 7-10 days at about 28° C., the shoot tips and nodal segments were transferred to fresh Medium A agar plates supplemented with 250 ppm cefotoxime. This transfer procedure was repeated 3 times.

C. Propagation of sterile plants in vitro

Explants which showed no signs of contamination were grown on agar containing MS medium supplemented with 500 ppm casein-hydrolysate, and 0.5-1.0 ppm BA for adventitious bud proliferation (Dodds). The individual buds which formed were cultured on agar plates containing MS medium supplemented with 0.15 ppm each of NAA and BA or kinetin for plant development. The above disinfestation procedure yielded about 80% bacteria-free explants.

EXAMPLE 2

Callus Induction—Method 1

A. Callus induction

Aerial root tips, 1–2 cm long, were cut from the sterile explants from Example 1, and surface sterilized with 10% Clorox ® solution for 1–2 minutes, followed by 3 rinses in sterile distilled water. The root sections were cut into 3–4 mm segments, and the segments were individually cultured on 0.8% agar containing MS medium supplemented with 1 ppm each of 2,4-D and BA. A total of about 3,000 root segments from each of the *V. fragrans* and *V. phaeantha* plants were cultured.

After about 4 weeks in culture, at 28° C. and under ambient atmosphere, most of the segments showed elongation of the root tips. These swelled root segments were transferred 2–3 times to fresh solid medium containing MS and 1 ppm each of 2,4-D and BA, about 2–3 weeks per transfer, producing a small number of root segments (about 3 out of a total of the 3,000 cultured) which showed callus formation. Calli from both vanilla plant species were obtained in this manner.

B. First liquid-medium culture

The swollen root segment calli obtained as above were suspended in liquid MS medium containing 1 ppm 2,4-D and BA, and cultured in this medium, at about 28° C., for 2 weeks, under ambient atmosphere, then transferred 1–2 times to fresh liquid medium having the same composition. No growth of the callus was observed during the culture period.

C. Second solid-medium culture

Following the first liquid medium culture, the root tip calli were transferred to 0.8% agar containing MS medium, pH 5.8 with 3% sucrose, the vitamin mix given in Table 1 below, and one of the combinations of plant growth hormones listed in Table 2. The calli were cultured in subdued light at about 28° C., under ambient atmosphere, and subcultured approximately every 4–6 weeks, a total of 1–4 times. The calli grew about 300% during the solid-medium culture step.

TABLE 1

|  | mg/L |  | mg/L |
| --- | --- | --- | --- |
| myo-inositol | 100 | D-Ca-Pantothenate | 0.5 |
| Nicotinic acid | 2.5 | Riboflavin | 0.25 |
| Pyridoxine.HCl | 1.0 | Ascorbic Acid | 0.5 |
| Thiamine.HCl | 10.0 | Choline chloride | 0.1 |
| Glycine | 0.5 | L-cysteine HCl | 1.0 |
| Folic Acid | 0.5 | Malic Acid (monosodium salt) | 10.0 |
| D-Biotin | 0.05 | Casein Hydrolysate | 50.0 |

TABLE 2

| 5 uM 2,4-D + 5 uM BA |
| --- |
| 5 uM 2,4-D + 1 uM BA |
| 20 uM 2,4-D + 5 uM kinetin |
| 10 uM 2,4-D + 1 uM kinetin |

D. Second liquid-culture

The calli from the second solid-medium culture were teased apart, or chopped, depending on consistency, to approximately 0.5–1 gram pieces, and these were transferred to 250 ml Erlenmeyer flasks, and covered with 50 ml liquid medium identical to that in IIC, except for the absence of agar. The flasks were covered with a sterile cap, and incubated with stirring for 30 days under ambient atmosphere. Stirring speed was about 150 rpm, and incubation temperature was between about 24°–30° C. The callus clumps are reduced slowly under these conditions to small, multi-cell particles consisting of less than about 10 cells/particle.

Before the stationary phase was reached (about 2 weeks in liquid culture), the cells were examined for cell viability, according to the method below. If cell viability was greater than about 25%, and if the cell suspension revealed an increase in cell density, the fine multi-cell particles were drawn off by pipetting, condensed by low-speed centrifugation, and added to fresh liquid culture for subculturing under the above conditions. Larger cell clumps remaining in the original culture were broken down by addition of fresh medium to the clumps remaining in the flasks, and further stirring under the same culture conditions. The cells are assayed for viability as above, and small multi-cellular particles from the two subculture groups are drawn off, condensed, and subcultured in fresh medium as above. The fine-particle suspension of cells can be subcultured in this fashion until a desired number of cells is achieved.

E. Testing cell viability

Cell viability of the callus cell suspension was examined by dye exclusion of a fluorescent dye. A stock solution of fluorescein diacetate (FDA) stain (5 mg FDA/ml acetone), was diluted 1:50 with cell culture medium and one drop of the diluted stain added to one drop of cell suspension on a microscope slide. Viable and non-viable cells were counted by fluorescence microscopy.

EXAMPLE 3

Callus Induction—Method 2

A. Seed germination

Individuals beans of *V. fragrans,* and *V. phaeantha* were washed thoroughly in distilled water, then soaked in 1% Alconox solution for 20 minutes with occasional shaking. After rinsing three times with distilled water, the seeds were soaked in a 10% Clorox ® solution for 20 minutes with occasional shaking, then rinsed 3 times with sterile distilled water.

The sterilized seed-sods were cut in half longitudinally, and seeds cultured with placental residues and sticky fatty materials with 95% alcohol on Knudson medium, supplemented with 10% fresh coconut water. The seed cultures were maintained at 32° C. in the dark for periods up to 4 months. The first evidence of seed germination is the rupture of the black seed coat, followed by protrusion of the spherical and then cone-shaped embryo, and subsequent formation of a cone-shaped protocorm. The percentage of seeds which germinated was about 6%.

B. Callus formation

After germination, the seeds from above are transferred to fresh agar plates containing Knudson medium supplemented with the vitamin mixture given in Table 1 above, and a growth hormone mixture containing various combinations of 2,4-D and BA. The seeds are grown in subdued light at 32° C. for a period of about 4 weeks, under ambient atmosphere. During the period of growth and development, numerous rhizoids formed from the epidermal formed from the epidermal cells of embryos and leaf primordia on the top of the cone-shaped protocorms.

Segments of leaf primordia cut from the tops of the protocorms, and rhizoid tip segments cut from the developing protocorms (each about 2 mm in length) are individually cultured on 0.8% agar containing MS medium supplemented with 1 ppm each of 2,4-D and BA.

After about 4 weeks in culture, the leaf primordia and rhizoid segments are transferred 2-3 times to fresh solid medium containing MS and 1 ppm each of 2,4-D and BA, about 2-3 weeks per transfer, producing a small number of segments which showed callus formation.

C. Liquid-culture

The calli from the solid-medium culture are teased apart, or chopped, depending on consistency, to approximately 0.5-1 gram pieces. These cells are transferred to 250 ml Erlenmeyer flasks, and covered with 50 ml liquid medium identical to that in IIC, except for the absence of agar. The callus cells are cultured as in Example 2.

EXAMPLE 4

Producing Vanilla Flavor Composition

The cultured callus cells from Example 2 were grown to a cell concentration of about 12 g dry weight per liter culture volume, and 10 ml of the cells were added to 50 ml MS medium containing the vitamin mixture (Table I) and 30 g/l sucrose in a 125 ml Erlenmeyer flask. The resin (5 g of XAD-4 resin) was added to the flask. The resin was washed with methanol and dried under vacuum prior to use. The flask was incubated for 6 days at 26° C. in the dark at an agitation speed of 150 rpm. The flask contents were harvested and analyzed for vanillin and other vanilla flavor components as described in Example 7. About 55 mcg of flavor material was detected in 60 ml of culture mixture.

EXAMPLE 5

Producing Vanilla Flavor Composition

The cultured cells from Example 2 were grown to a cell density of about 12 g per liter and 10 ml of the cells were added to a 125 ml Erlenmeyer flask containing 50 ml MS medium, vitamin mixture (Table I) and 30 g/l lactose. Washed XAD-4 resin (5 g) was added to the culture. The flask was incubated for 29 days at 26° C. in the dark at an agitation speed of 150 rpm. On day 29, 5 ml of the culture resin mixture was withdrawn for analysis and replaced with 5 g of washed XAD-4 resin. On day 38, a second sample was taken and 5 more g of XAD-4 resin was added. The final sample was taken at day 47 when the culture was terminated. Analysis for vanillin and vanilla flavor components was performed as described in Example 7. About 900 mcg of flavor material was detected in 50 ml of culture medium. Results were as follows:

| Time (days) | Vanillin (mg/l) |
| --- | --- |
| 29 | 1.8 |
| 38 | 9.7 |
| 47 | 18.0 |

EXAMPLE 6

Flavor Production in a Reactor System

The cultured callus cells from Example 2 were grown to a cell density of 7-8 g/l in 7 days. Approximately proximately 75 ml of the cell suspension were mixed with 35 ml of 2.4% sodium alginate solution and pipetted dropwise into 250 ml of 3% w/v calcium chloride solution. Formation of calcium alginate beads (containing cells) ensued; these beads were cured in 3% w/v calcium chloride solution for 2 hours. Beads were washed twice in (phosphate deficient) MS medium.

The beads were packed into a 2.5 cm diameter reactor to a final height of 8 cm. Aerated medium, containing 3% sucrose, vitamin mix, minus potassium phosphate was circulated through the reactor bed at a flow rate of 100 ml/min. Circulation loop included one column containing 13 grams of XAD-4 resin.

At the end of day 5, circulation was diverted from the first XAD-4 column to a second, identical column containing XAD-4 resin. Circulation was continued for 8 days.

Analysis for vanillin and vanilla flavor components was performed as described in Example 7. Results were as follows:

| | Column 1 (mcg) | Column 2 (mcg) |
| --- | --- | --- |
| 1. Vanillin | 52 | 41 |
| 2. Vanillyl alcohol | 2.8 | 13 |
| | | (total for 2-5) |
| 3. 4-hydroxybenzaldehyde | 2.5 | |
| 4. 4-hydroxybenzoic acid | 4.9 | |
| 5. Vanillic acid | 6.0 | |

EXAMPLE 7

HPLC Characterization of Vanilla Flavors

HPLC analysis of the vanilla flavor material obtained in Example 4 was performed by HPLC, using a 4.6 mm id × 15 cm HPLC column packed with octadecylsilyl reverse-phase packing material. The extracted vanilla material was dissolved in 50% methanol, final concentration 10 mg/ml, and 10 lambda of the solution was applied to the column. The material was eluted with a linear gradient from 5% methanol to 25% methanol containing 0.5% acetic acid. The column peaks were monitored at 280 nm.

The chromatogram is shown in FIG. 3B. For comparison, a chromatogram obtained by identical HPLC analysis of commercial vanilla bean extract, diluted 1:20, is shown in FIG. 3A. The peak identities, as determined by spectral character and external standards are shown in the figure.

As seen, the vanilla flavor extract contains a high percentage of vanillin, relatively low amounts of the compounds associated with peaks 1-7, and relatively large amounts of slower eluting material.

Although the invention has been described with respect to particular methods and products, it will be apparent that various changes and modifications may be made without departing from the invention.

It is claimed:

1. Callus cells which are independent of and unattached to differentiated plant tissue, and which (a) are derived from vanilla plant tissue, (b) are capable of growth in cell culture without forming identifiable differentiated cell structures, and (c) secrete vanillin and related vanilla flavor components into culture medium in which the cells are cultured.

2. The cells of claim 1, wherein the cells are derived from vanilla plant root tissue material, and said vanilla flavor components include 3,4-dihydroxybenzaldehyde, 4-hydroxybenzoic acid, 4-hydroxybenzaldehyde and vanillic acid.

3. The cells of claim 1, which are identified by ATCC #40354.

* * * * *